(12) United States Patent
Miller et al.

(10) Patent No.: US 10,357,056 B2
(45) Date of Patent: Jul. 23, 2019

(54) **ENDOLYSIN FROM BACTERIOPHAGE AGAINST *GEOBACILLUS* AND METHODS OF USING**

(71) Applicant: ALTRIA CLIENT SERVICES LLC, Richmond, VA (US)

(72) Inventors: Elisabeth Miller, Chesterfield, VA (US); Ujwala Warek, Chester, VA (US); Dongmei Xu, Glen Allen, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 593 days.

(21) Appl. No.: 15/009,933

(22) Filed: Jan. 29, 2016

(65) Prior Publication Data

US 2016/0219925 A1    Aug. 4, 2016

Related U.S. Application Data

(60) Provisional application No. 62/109,156, filed on Jan. 29, 2015.

(51) Int. Cl.
| | | |
|---|---|---|
| *C12N 7/00* | (2006.01) | |
| *C12N 9/80* | (2006.01) | |
| *A01N 63/00* | (2006.01) | |
| *A24B 15/18* | (2006.01) | |
| *A24B 15/20* | (2006.01) | |
| *A24B 15/24* | (2006.01) | |
| *A24B 15/30* | (2006.01) | |
| *C07K 14/005* | (2006.01) | |

(52) U.S. Cl.
CPC ............ *A24B 15/307* (2013.01); *A01N 63/00* (2013.01); *A24B 15/183* (2013.01); *A24B 15/20* (2013.01); *A24B 15/245* (2013.01); *A24B 15/30* (2013.01); *C07K 14/005* (2013.01); *C12N 7/00* (2013.01); *C12N 9/80* (2013.01); *C12N 2795/00021* (2013.01); *C12N 2795/00022* (2013.01); *C12N 2795/00031* (2013.01)

(58) Field of Classification Search
None
See application file for complete search history.

(56) References Cited

U.S. PATENT DOCUMENTS

| | | |
|---|---|---|
| 4,528,993 A | 7/1985 | Sensabaugh et al. |
| 4,660,577 A | 4/1987 | Sensabaugh et al. |
| 4,848,373 A | 7/1989 | Lenkey et al. |
| 5,204,257 A | 4/1993 | DeBonville et al. |
| 5,372,149 A | 12/1994 | Roth et al. |
| 5,447,836 A | 9/1995 | Wolber et al. |
| 5,660,812 A | 8/1997 | Merril et al. |
| 5,688,501 A | 11/1997 | Merril et al. |
| 5,712,089 A | 1/1998 | Borrebaeck et al. |
| 5,723,330 A | 3/1998 | Rees et al. |
| 5,766,892 A | 6/1998 | Merril et al. |
| 5,811,093 A | 9/1998 | Merril et al. |
| 5,914,240 A | 6/1999 | Sanders |
| 5,958,675 A | 9/1999 | Wicks et al. |
| 6,027,930 A | 2/2000 | Borrebaeck et al. |
| 6,056,954 A | 5/2000 | Fischetti et al. |
| 6,090,541 A | 7/2000 | Wicks et al. |
| 6,121,036 A | 9/2000 | Ghanbari et al. |
| 6,190,856 B1 | 2/2001 | Li |
| 6,238,661 B1 | 5/2001 | Fischetti et al. |
| 6,248,324 B1 | 6/2001 | Fischetti et al. |
| 6,254,866 B1 | 7/2001 | Fischetti et al. |
| 6,264,945 B1 | 7/2001 | Fischetti et al. |
| 6,265,169 B1 | 7/2001 | Cortese et al. |
| 6,277,399 B1 | 8/2001 | Fischetti et al. |
| 6,326,002 B1 | 12/2001 | Fischetti et al. |
| 6,335,012 B1 | 1/2002 | Fischetti et al. |
| 6,395,504 B1 | 5/2002 | Trudil |
| 6,432,444 B1 | 8/2002 | Fischetti et al. |
| 6,436,661 B1 | 8/2002 | Adams et al. |
| 6,448,083 B1 | 9/2002 | Larocca et al. |
| 6,555,331 B1 | 4/2003 | Hyman et al. |
| 6,635,238 B2 | 10/2003 | Delisle |
| 6,685,937 B2 | 2/2004 | Fischetti et al. |
| 6,699,701 B1 | 3/2004 | Sulakvelidze et al. |
| 6,737,079 B2 | 5/2004 | Fischetti et al. |
| 6,759,229 B2 | 7/2004 | Schaak |
| 6,783,930 B1 | 8/2004 | Pelletier et al. |
| 6,896,882 B2 | 5/2005 | Ramachandran et al. |
| 6,919,075 B1 | 7/2005 | Soloman et al. |
| 6,936,244 B2 | 8/2005 | Fiochetti et al. |
| 6,942,858 B1 | 9/2005 | Ghanbari et al. |
| 6,955,893 B2 | 10/2005 | Delisle |
| 7,063,837 B2 | 6/2006 | Fischetti et al. |
| 7,087,226 B2 | 8/2006 | Ramachandran et al. |
| 7,128,916 B2 | 10/2006 | March |

(Continued)

FOREIGN PATENT DOCUMENTS

| | | |
|---|---|---|
| WO | WO 2009/012481 | 1/2009 |
| WO | WO 2014/150870 | 9/2014 |

OTHER PUBLICATIONS

Gill et al. Bacteriophage Ecology and Plants (2003) in APSnet; pp. 1-17 (Year: 2003).*

Krawczyk et al. Draft genome sequences of four bacillus thermoamylovorans strains isolated from milk and acacia gum, a food ingredient (2015) GenomeA; vol. 3, pp. 1-2 (Year: 2015).*

Frampton et al. Advances in bacteriophage-mediated control of plant pathogens. (2012) International Journal of Microbiology; vol. 2012; pp. 1-11 (Year: 2012).*

Database accession No. AOAODOF4B8, Database UniProt [Online] Apr. 29, 2015, "Full=Phage N-acetylrnurarnoyl-L-alanine arnidase, {EC0:00003131EMBL:KI060252.1}; EC~3.5.1.28 {EC0:0000313!EMBL:KI060252.1})," retrieved from http://ibis/exam/dbfetch.jsp?id=UNIPROT:AOAODOF4B8, 1 page.

(Continued)

*Primary Examiner* — Cathy Kingdon Worley

(74) *Attorney, Agent, or Firm* — Arnold & Porter Kaye Scholer LLP

(57) ABSTRACT

Bacteriophage against *Geobacillus* are provided, and methods of making and using the bacteriophage also are provided.

13 Claims, 1 Drawing Sheet

Specification includes a Sequence Listing.

(56) References Cited

U.S. PATENT DOCUMENTS

| | | | |
|---|---|---|---|
| 7,141,241 | B2 | 11/2006 | Fischetti et al. |
| 7,169,408 | B2 | 1/2007 | Fischetti et al. |
| 7,244,612 | B2 | 7/2007 | Goodridge |
| 7,276,332 | B2 | 10/2007 | Goodridge |
| 7,332,307 | B2 | 2/2008 | Carlton et al. |
| 7,459,272 | B2 | 12/2008 | Morris et al. |
| 7,588,929 | B2 | 9/2009 | Bujanover |
| 7,632,637 | B1 | 12/2009 | Boss et al. |
| 7,687,069 | B2 | 3/2010 | Fischetti et al. |
| 7,694,686 | B2 | 4/2010 | Breslin et al. |
| 7,951,579 | B2 | 5/2011 | Hargis et al. |
| 7,985,573 | B2 | 7/2011 | Yacoby et al. |
| 8,003,323 | B2 | 8/2011 | Morris et al. |
| 8,092,990 | B2 | 1/2012 | Voorhees |
| 2004/0118422 | A1 | 6/2004 | Lundin et al. |
| 2005/0178398 | A1 | 8/2005 | Breslin et al. |
| 2005/0244521 | A1 | 11/2005 | Strickland et al. |
| 2006/0191548 | A1 | 8/2006 | Strickland et al. |
| 2009/0036307 | A1 | 2/2009 | Gabriel |
| 2010/0116281 | A1 | 5/2010 | Marshall et al. |
| 2010/0203180 | A1 | 8/2010 | Yoon et al. |
| 2012/0024301 | A1 | 2/2012 | Carroll et al. |
| 2012/0031414 | A1 | 2/2012 | Atchley et al. |
| 2012/0031416 | A1 | 2/2012 | Atchley et al. |

OTHER PUBLICATIONS

Jin et al., "Roles of bacteriophage GVE2 endolysin in host lysis at high temperatures," Microbiology, 2013, 159:1597-1605.

Schmelcher et al., "Bacteriophage endolysins as novel antimicrobials," Future Microbiology, 2012, 7(10):1147-1171.

International Search Report and Written Opinion in International Application No. PCT/US2016/015516, dated Jun. 2, 2016, 14 pages.

International Search Report and Written Opinion in International Application No. PCT/US2016/015520, dated Jun. 22, 2016, 16 pages.

Dorval-Couchesne et al., "Production and Application of Bacteriophage and Bacteriophage-Encoded Lysins," *Recent Patents on Biotechnology*, 2009, 3:37-45.

Hawtrey et al., "Isolation, Characterization, and Annotation: The Search for Novel Bacteriophage Genomes," *The Journal of Experimental Secondary Science*, 2012, 1-9.

Hendrix et al., "Evolutionary relationships among diverse bacteriophages and prophages: all the world's a phage," *PNAS USA*, 1999, 96:2192-7.

International Preliminary Report on Patentability in International Application No. PCT/US2014/024432, dated Jul. 7, 2015, 10 pages.

International Search Report and Written Opinion in International Application No. 2014/024432, dated Nov. 3, 2014, 18 pages.

Invitation to Pay Fees in International Application No. PCT/US2014/024432, dated Sep. 15, 2014, 8 pages.

Invitation to Pay Fees in International Application No. PCT/US2016/015520, dated Apr. 15, 2016, 7 pages.

Loessner et al., "C-terminal domains of Listeria monocytogenes bacteriophage murein hydrolases determine specific recognition and high-affinity binding to bacterial cell wall carbohydrates," Mol. Microbiol., 2002, 44:335-49.

Ozawa et al., "Bacteriophage P4282, a parasite of Ralstonia solanacearum, encodes a bacteriolytic protein important for lytic infection of its host," Molecular Genetics and Genomics, 2001, 265.1: 95-101.

Pope et al., "Expanding the Diversity of Mycobacteriophages: Insights into Genome Architecture and Evolution," *PLoS One*, Jan. 2011, 6(1):1-20.

Seeley and Primrose, "A Review: The isolation of bacteriophages from the environment," *J. Applied Bacteriology*, 1982, 53:1-17.

Son et al., "Antibacterial and biofilm removal activity of a podoviridae Staphylococcus aureus bacteriophage SAP-2 and a derived recombinant cell-wall-degrading enzyme," Applied Microbiology and Biotechnology, Dec. 2009, 86(5):1439-1449.

Takac, "Functional analysis of the lysis genes of Staphylococcus aureus phage P68 in Escherichia coli," Microbiology, Jul. 2005, 151(7):2331-2342.

Tanaka et al., "Control of tobacco bacterial wilt by an avirulent strain of Pseudomonas solanacearum M4S and its bacteriophage," Ann. Phytopath. Soc. Japan, Jan. 1990, 56:243-246.

Tso, "Seed to Smoke," Tobacco, Production, Chemistry and Technology, Davis & Nielsen, eds., 1999, Chapter 1, 33 pages.

Vybiral et al., "Complete nucleotide sequence and molecular characterization of two lytic Staphylococcus aureus phages: 44AHJD and P68," FEMS Microbiology Letters, Feb. 2003, 219(2):275-283.

International Preliminary Report on Patentability in International Application No. PCT/US2016/015516, dated Aug. 1, 2017, 7 pages.

\* cited by examiner

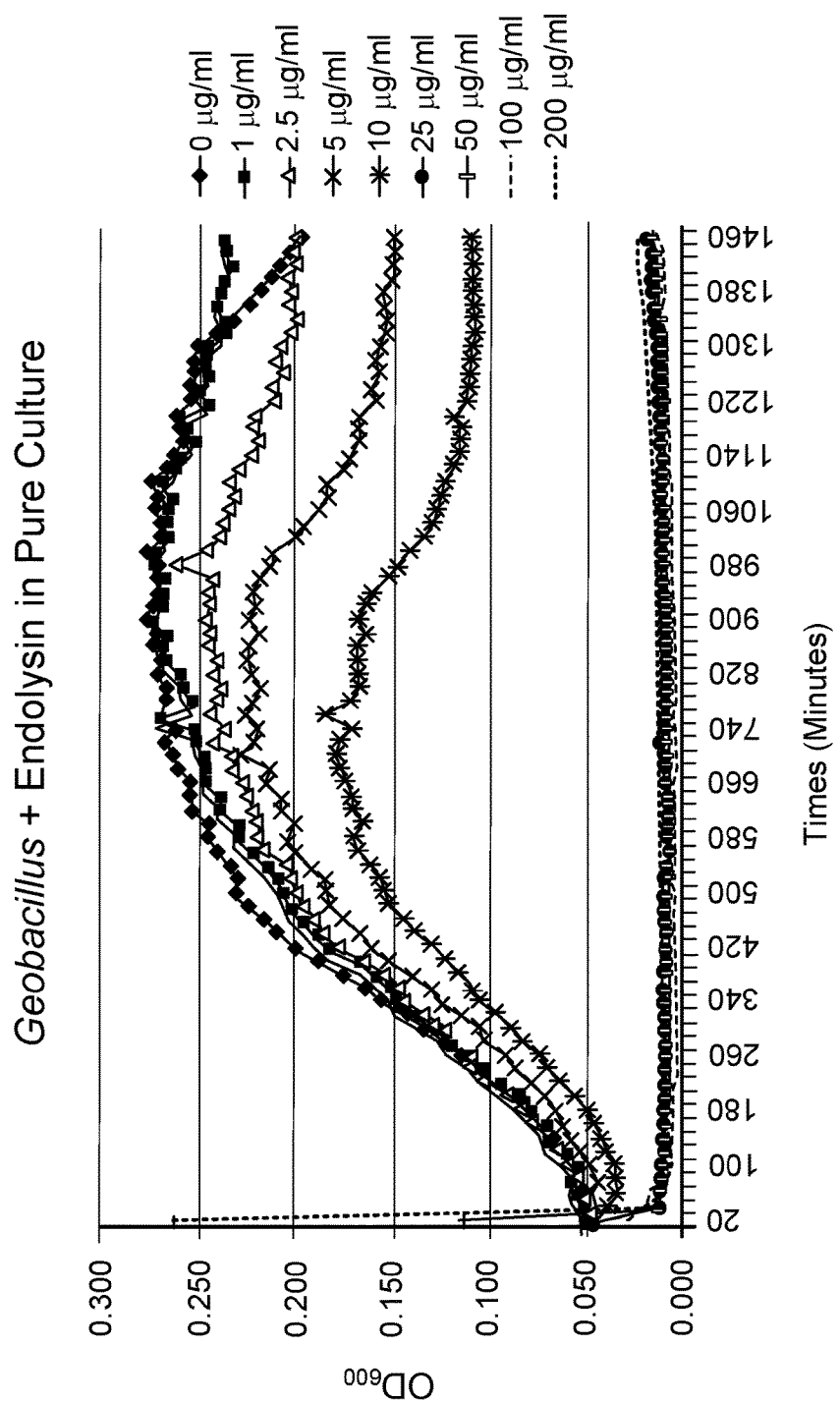

SEQUENCE LISTING

```
<160> NUMBER OF SEQ ID NOS: 12

<210> SEQ ID NO 1
<211> LENGTH: 993
<212> TYPE: DNA
<213> ORGANISM: Artificial Sequence
<220> FEATURE:
<223> OTHER INFORMATION: Bacteriophage against Geobacillus sp. strain
      G05

<400> SEQUENCE: 1
atggtaaaaa tcagacaaat gctagtatcg ccgaaaaaat accgtattaa atgcccgtac     60
gaaatgacgc ctgaatatat cactgtccac aacacagcca acgacgcaag cgccaacaac    120
gaagtacagt acatgatcaa taacagcaat caagtatcat accatattgc agttgacgac    180
gtggaggcgg tacaagggtt gccgctagac cgcaacggtt ggcacagtgg agacggaaac    240
gggccgggaa accgtaaatc aatcggagta gaaatttgct actcgaggtc aggcggcgag    300
cgatacagaa aagccgaaca aaacgctatt aaacttatcg cacaactcct gagagagcgc    360
```

```
ggatggggga ttgaccgcgt gaaaaaacat caagattggt cggggaaata ttgcccacac    420
cgtattttag acgaaggtcg ttgggaatca tttaaagcgg aaatacaaaa ggaattaacc    480
ggacaacctg ctgcgccggt cacaccatca accggtaata tcggcgttgg ctctatcgtc    540
actgtagccg cacatgcaac gcattatcag accgggcaac cgatagctag ctttgtcaag    600
ggcaaccggt acaaagtcat acaagtaaaa gatgtacgtg gcggtaacag taccaaggct    660 ttttgctcg acggtattat gtcgtgggtg tgggagcagg atattgtcga ggcgggcgga    720
caagcggtag caccgcaacc gcaggcaaag aaacggtata tcgtgttacc agcaaacgcc    780
acaagttgga cggtgtacaa gctcgacaga ccaccagtca aggcgaacaa agcaaatatc    840
gcagggacgt tgagaccgtc aaaatttggt gggttaacat atgaaatact tgaggacctt    900
ggcggacacg tttataaaat caggacagga gatttggct tggtaaaaat ttacggtgcg    960
ccaagtacag gggcacggat tgtggaaaaa taa                                 993
```

<210> SEQ ID NO 2
<211> LENGTH: 330
<212> TYPE: PRT
<213> ORGANISM: Artificial Sequence
<220> FEATURE:
<223> OTHER INFORMATION: Bacteriophage against Geobacillus sp. strain
      G05

<400> SEQUENCE: 2

```
Met Val Lys Ile Arg Gln Met Leu Val Ser Pro Lys Lys Tyr Arg Ile
1               5                   10                  15

Lys Cys Pro Tyr Glu Met Thr Pro Glu Tyr Ile Thr Val His Asn Thr
                20                  25                  30

Ala Asn Asp Ala Ser Ala Asn Asn Glu Val Gln Tyr Met Ile Asn Asn
            35                  40                  45

Ser Asn Gln Val Ser Tyr His Ile Ala Val Asp Asp Val Glu Ala Val
        50                  55                  60

Gln Gly Leu Pro Leu Asp Arg Asn Gly Trp His Ser Gly Asp Gly Asn
65                  70                  75                  80

Gly Pro Gly Asn Arg Lys Ser Ile Gly Val Glu Ile Cys Tyr Ser Arg
                85                  90                  95

Ser Gly Gly Glu Arg Tyr Arg Lys Ala Glu Gln Asn Ala Ile Lys Leu
                100                 105                 110

Ile Ala Gln Leu Leu Arg Glu Arg Gly Trp Gly Ile Asp Arg Val Lys
            115                 120                 125

Lys His Gln Asp Trp Ser Gly Lys Tyr Cys Pro His Arg Ile Leu Asp
    130                 135                 140

Glu Gly Arg Trp Glu Ser Phe Lys Ala Glu Ile Gln Lys Glu Leu Thr
145                 150                 155                 160

Gly Gln Pro Ala Ala Pro Val Thr Pro Ser Thr Gly Asn Ile Gly Val
                165                 170                 175

Gly Ser Ile Val Thr Val Ala Ala His Ala Thr His Tyr Gln Thr Gly
            180                 185                 190

Gln Pro Ile Ala Ser Phe Val Lys Gly Asn Arg Tyr Lys Val Ile Gln
        195                 200                 205

Val Lys Asp Val Arg Gly Gly Asn Ser Thr Lys Ala Phe Leu Leu Asp
    210                 215                 220

Gly Ile Met Ser Trp Val Trp Glu Gln Asp Ile Val Glu Ala Gly Gly
225                 230                 235                 240
```

-continued

```
Gln Ala Val Ala Pro Gln Pro Gln Ala Lys Lys Arg Tyr Ile Val Leu
                245                 250                 255

Pro Ala Asn Ala Thr Ser Trp Thr Val Tyr Lys Leu Asp Arg Pro Pro
            260                 265                 270

Val Lys Ala Asn Lys Ala Asn Ile Ala Gly Thr Leu Arg Pro Ser Lys
        275                 280                 285

Phe Gly Gly Leu Thr Tyr Glu Ile Leu Glu Asp Leu Gly Gly His Val
    290                 295                 300

Tyr Lys Ile Arg Thr Gly Asp Phe Gly Leu Val Lys Ile Tyr Gly Ala
305                 310                 315                 320

Pro Ser Thr Gly Ala Arg Ile Val Glu Lys
                325                 330

<210> SEQ ID NO 3
<211> LENGTH: 993
<212> TYPE: DNA
<213> ORGANISM: Artificial Sequence
<220> FEATURE:
<223> OTHER INFORMATION: Bacteriophage against Geobacillus sp. strain
      G08

<400> SEQUENCE: 3
gtaaaaatca gacaaatgct agtatcgccg aaaaaatacc gtattaaatg cccgtacgaa      60
atgacgcctg aatatatcac tgtccacaac acagccaacg acgcaagcgc caacaacgaa     120
gtacagtaca tgatcaataa cagcaatcaa gtatcatacc atattgcagt tgacgacgtg     180
gaggcggtac aagggttgcc gctagaccgc aacggttggc acagtggaga cggaaacggg     240
ccgggaaacc gtaaatcaat cggagtagaa atttgctact cgaggtcagg cggcgagcga     300
tacagaaaag ccgaacaaaa cgctattaaa cttatcgcac aactcctgag agagcgcgga     360
tgggggattg accgcgtgaa aaaacatcaa gattggtcgg ggaaatattg cccacaccgt     420
attttagacg aaggtcgttg ggaatcattt aaagcgaaaa tacaaaagga attaaccgga     480
caacctgctg cgccggtcac accatcaacc ggtaatatcg gcgttggctc tatcgtcact     540
gtagccgcac atgcaacgca ttatcagacc gggcaaccga tagctagctt tgtcaagggc     600
aaccggtaca aagtcataca agtaaaagat gtacgtggcg gtaacagtac caaggctttt     660
ttgctcgacg gtattatgtc gtgggtgtgg gagcaggata ttgtcgaggc gggcggacaa     720
gcggtagcac cgcaaccgca ggcaaagaaa cggtatatcg tgttaccagc aaacgccaca     780
agttggacgg tgtacaagct cgacagacca ccagtcaagg cgaacaaagc aaatatcgca     840
gggacgttga ccgtcaaa atttggtggg ttaacatatg aaatacttga ggaccttggc     900
ggacacgttt ataaaatcag gacaggagat tttggcttgg taaaaattta cggtgcgcca     960
agtacagggg cacggattgt ggaaaaataa aag                                  993

<210> SEQ ID NO 4
<211> LENGTH: 329
<212> TYPE: PRT
<213> ORGANISM: Artificial Sequence
<220> FEATURE:
<223> OTHER INFORMATION: Bacteriophage against Geobacillus sp. strain
      G08

<400> SEQUENCE: 4

Val Lys Ile Arg Gln Met Leu Val Ser Pro Lys Lys Tyr Arg Ile Lys
1               5                   10                  15

Cys Pro Tyr Glu Met Thr Pro Glu Tyr Ile Thr Val His Asn Thr Ala
            20                  25                  30
```

Asn Asp Ala Ser Ala Asn Asn Glu Val Gln Tyr Met Ile Asn Asn Ser
         35                  40                  45

Asn Gln Val Ser Tyr His Ile Ala Val Asp Asp Val Glu Ala Val Gln
 50                  55                  60

Gly Leu Pro Leu Asp Arg Asn Gly Trp His Ser Gly Asp Gly Asn Gly
 65                  70                  75                  80

Pro Gly Asn Arg Lys Ser Ile Gly Val Glu Ile Cys Tyr Ser Arg Ser
                 85                  90                  95

Gly Gly Glu Arg Tyr Arg Lys Ala Glu Gln Asn Ala Ile Lys Leu Ile
                100                 105                 110

Ala Gln Leu Leu Arg Glu Arg Gly Trp Gly Ile Asp Arg Val Lys Lys
                115                 120                 125

His Gln Asp Trp Ser Gly Lys Tyr Cys Pro His Arg Ile Leu Asp Glu
        130                 135                 140

Gly Arg Trp Glu Ser Phe Lys Ala Glu Ile Gln Lys Glu Leu Thr Gly
145                 150                 155                 160

Gln Pro Ala Ala Pro Val Thr Pro Ser Thr Gly Asn Ile Gly Val Gly
                165                 170                 175

Ser Ile Val Thr Val Ala Ala His Ala Thr His Tyr Gln Thr Gly Gln
                180                 185                 190

Pro Ile Ala Ser Phe Val Lys Gly Asn Arg Tyr Lys Val Ile Gln Val
                195                 200                 205

Lys Asp Val Arg Gly Gly Asn Ser Thr Lys Ala Phe Leu Leu Asp Gly
        210                 215                 220

Ile Met Ser Trp Val Trp Glu Gln Asp Ile Glu Ala Gly Gly Gln
225                 230                 235                 240

Ala Val Ala Pro Gln Pro Gln Ala Lys Lys Arg Tyr Ile Val Leu Pro
                245                 250                 255

Ala Asn Ala Thr Ser Trp Thr Val Tyr Lys Leu Asp Arg Pro Pro Val
                260                 265                 270

Lys Ala Asn Lys Ala Asn Ile Ala Gly Thr Leu Arg Pro Ser Lys Phe
        275                 280                 285

Gly Gly Leu Thr Tyr Glu Ile Leu Glu Asp Leu Gly Gly His Val Tyr
                290                 295                 300

Lys Ile Arg Thr Gly Asp Phe Gly Leu Val Lys Ile Tyr Gly Ala Pro
305                 310                 315                 320

Ser Thr Gly Ala Arg Ile Val Glu Lys
                325

<210> SEQ ID NO 5
<211> LENGTH: 993
<212> TYPE: DNA
<213> ORGANISM: Artificial Sequence
<220> FEATURE:
<223> OTHER INFORMATION: Bacteriophage against Geobacillus sp. strain
      G09

<400> SEQUENCE: 5
atggtaaaaa tcagacaaat gctagtatcg ccgaaaaaat accgtattaa atgcccgtac     60
gaaatgacgc ctgaatatat cactgtccac aacacagcca acgacgcaag cgccaacaac    120
gaagtacagt acatgatcaa taacagcaat caggtatcat accatattgc agttgacgac    180
gtggaggcgg tacaagggtt gccgctagac cgcaacggtt ggcacagtgg agacggaaac    240
gggccgggaa accgtaaatc aatcggagta gaaatttgct actcgaggtc aggcggcgag    300

```
cgatacagaa aagccgaaca aaacgctatt aaacttatcg cacaactcct gagagagcgc    360
ggatggggga ttgaccgcgt gaaaaaacat caagattggt cggggaaata ttgcccacac    420
cgtattttag acgaaggtcg ttgggaatca tttaaagcgg aaatacaaaa ggaattaacc    480
ggacaacctg ctgcgccggt cacaccatca aacggtaata tcggcgttgg ctctatcgtc    540
actgtagccg cacatgcaac gcactaccaa acaggacagc cgatagctag ctttgtcaag    600
ggcaaccggt ataaagtgat acaagtaaaa gatgtacgtg gcggtaacag taccaaggcc    660
ttttttgctcg acggtattat gtcgtgggtg tgggagcagg atattgtcga ggcgggcgga    720
caagcggtag caccgcaacc gcaggcaaag aaacggtata tcgtgttacc agcaaacgcc    780
acaagttgga cggtgtacaa gctcgacaga ccaccagtca aggcgaacaa agcaaatatc    840
gcagggacgt tgagaccgtc aaaatttggt gggttaacat atgaaatact tgaggacctt    900
ggcggacacg tttataaaat caggacagga gattttggct tggtaaaaat ttacggtgcg    960
ccaagtacag gggcacggat tgtggaaaaa taa                                 993
```

<210> SEQ ID NO 6
<211> LENGTH: 330
<212> TYPE: PRT
<213> ORGANISM: Artificial Sequence
<220> FEATURE:
<223> OTHER INFORMATION: Bacteriophage against Geobacillus sp. strain G09

<400> SEQUENCE: 6

```
Met Val Lys Ile Arg Gln Met Leu Val Ser Pro Lys Lys Tyr Arg Ile
1               5                   10                  15

Lys Cys Pro Tyr Glu Met Thr Pro Glu Tyr Ile Thr Val His Asn Thr
            20                  25                  30

Ala Asn Asp Ala Ser Ala Asn Asn Glu Val Gln Tyr Met Ile Asn Asn
        35                  40                  45

Ser Asn Gln Val Ser Tyr His Ile Ala Val Asp Asp Val Glu Ala Val
    50                  55                  60

Gln Gly Leu Pro Leu Asp Arg Asn Gly Trp His Ser Gly Asp Gly Asn
65                  70                  75                  80

Gly Pro Gly Asn Arg Lys Ser Ile Gly Val Glu Ile Cys Tyr Ser Arg
                85                  90                  95

Ser Gly Gly Glu Arg Tyr Arg Lys Ala Glu Gln Asn Ala Ile Lys Leu
            100                 105                 110

Ile Ala Gln Leu Leu Arg Glu Arg Gly Trp Gly Ile Asp Arg Val Lys
        115                 120                 125

Lys His Gln Asp Trp Ser Gly Lys Tyr Cys Pro His Arg Ile Leu Asp
    130                 135                 140

Glu Gly Arg Trp Glu Ser Phe Lys Ala Glu Gln Lys Glu Leu Thr
145                 150                 155                 160

Gly Gln Pro Ala Ala Pro Val Thr Pro Ser Asn Gly Asn Ile Gly Val
                165                 170                 175

Gly Ser Ile Val Thr Val Ala Ala His Ala Thr His Tyr Gln Thr Gly
            180                 185                 190

Gln Pro Ile Ala Ser Phe Val Lys Gly Asn Arg Tyr Lys Val Ile Gln
        195                 200                 205

Val Lys Asp Val Arg Gly Gly Asn Ser Thr Lys Ala Phe Leu Leu Asp
    210                 215                 220

Gly Ile Met Ser Trp Val Trp Glu Gln Asp Ile Val Glu Ala Gly Gly
225                 230                 235                 240
```

Gln Ala Val Ala Pro Gln Pro Gln Ala Lys Lys Arg Tyr Ile Val Leu
            245                 250                 255

Pro Ala Asn Ala Thr Ser Trp Thr Val Tyr Lys Leu Asp Arg Pro Pro
        260                 265                 270

Val Lys Ala Asn Lys Ala Asn Ile Ala Gly Thr Leu Arg Pro Ser Lys
    275                 280                 285

Phe Gly Gly Leu Thr Tyr Glu Ile Leu Glu Asp Leu Gly Gly His Val
290                 295                 300

Tyr Lys Ile Arg Thr Gly Asp Phe Gly Leu Val Lys Ile Tyr Gly Ala
305                 310                 315                 320

Pro Ser Thr Gly Ala Arg Ile Val Glu Lys
            325                 330

<210> SEQ ID NO 7
<211> LENGTH: 1110
<212> TYPE: DNA
<213> ORGANISM: Artificial Sequence
<220> FEATURE:
<223> OTHER INFORMATION: Bacteriophage against Geobacillus sp. strain
      G15

<400> SEQUENCE: 7
atggttaaat atatagttga cttgtcacac catcaagacc ctaaaaattt taattatgac        60
gtgtttgccc aaaacatccg tcatgccatt atccgtacac aatacggatc aaagacagtg       120
gatagacact acaaaacaca tcatgcagaa ctacgaaaaa ggggaatagg tacttcggca       180
tacgcatggg ttcgaggggt ttccgagaat gatatgcggg tagaagcgcg ggactttttt       240
aatcgtacaa aagatttgaa acctcttgca tgggtactag atgtagagga aaaagtatg       300 gcaaacatgc gggcagggt taaagcctac gttgatgagt taagaaaatt aggtgttaca       360
gaagagattg gtgtatacat tgcccatcat ctatacaagc cttttaattt agacctaaat       420
gactttgatt tgtttggat accgagatat ggagcaaaca acggtcaaat gcacgatacc       480
aaacctagct atccttgtga tctttggcag tttaccagtc aaggaagact agacggatat       540
aatggggtac tagacttaaa cgttgtggtt agcaataaac ctttacggtt tttacaaggt       600
gcacagccaa caccgcaacc aagtcctagc gggaatattg gcgttggttc tatcgtcact       660
gtagccgcac atgcaacgca ctaccaaaca ggacagccga tagcggattt tgtcaagggc       720
aaccggtaca gagtgataca agtaaaagat gtgcgtggcg gtaacagtac caaggccttt       780
ttgctagacg gtattatgtc gtgggtgtgg gagcaggata ttgtcgaggc gggcggacaa       840
gcggtagcac cgcaaccgca ggcaaagaaa tggtatatcg tgttaccagc aaacgccaca       900
agttggacgg tgtacaagct cgacagacca ccagtcaagg cgaacaaagc aaatatcgca       960
gggacgttga accgtcaaa atttggtggg ttaacatatg aaatacttga ggaccttggc      1020
ggacacgttt ataaaatcag gacaggagat tttggcttgg taaaaattta cggtgcgcca      1080
agtacaggag cgaggattgt ggaaaaataa                                      1110

<210> SEQ ID NO 8
<211> LENGTH: 369
<212> TYPE: PRT
<213> ORGANISM: Artificial Sequence
<220> FEATURE:
<223> OTHER INFORMATION: Bacteriophage against Geobacillus sp. strain
      G15

<400> SEQUENCE: 8

```
Met Val Lys Tyr Ile Val Asp Leu Ser His Gln Asp Pro Lys Asn
1               5                   10                  15

Phe Asn Tyr Asp Val Phe Ala Gln Asn Ile Arg His Ala Ile Ile Arg
                20                  25                  30

Thr Gln Tyr Gly Ser Lys Thr Val Asp Arg His Tyr Lys Thr His His
            35                  40                  45

Ala Glu Leu Arg Lys Arg Gly Ile Gly Thr Ser Ala Tyr Ala Trp Val
50                  55                  60

Arg Gly Val Ser Glu Asn Asp Met Arg Val Glu Ala Arg Asp Phe Phe
65                  70                  75                  80

Asn Arg Thr Lys Asp Leu Lys Pro Leu Ala Trp Val Leu Asp Val Glu
                85                  90                  95

Glu Lys Ser Met Ala Asn Met Arg Ala Gly Val Lys Ala Tyr Val Asp
                100                 105                 110

Glu Leu Arg Lys Leu Gly Val Thr Glu Glu Ile Gly Val Tyr Ile Ala
            115                 120                 125

His His Leu Tyr Lys Pro Phe Asn Leu Asp Leu Asn Asp Phe Asp Phe
        130                 135                 140

Val Trp Ile Pro Arg Tyr Gly Ala Asn Asn Gly Gln Met His Asp Thr
145                 150                 155                 160

Lys Pro Ser Tyr Pro Cys Asp Leu Trp Gln Phe Thr Ser Gln Gly Arg
                165                 170                 175

Leu Asp Gly Tyr Asn Gly Val Leu Asp Leu Asn Val Val Ser Asn
                180                 185                 190

Lys Pro Leu Arg Phe Leu Gln Gly Ala Gln Pro Thr Pro Gln Pro Ser
                195                 200                 205

Pro Ser Gly Asn Ile Gly Val Gly Ser Ile Val Thr Val Ala Ala His
        210                 215                 220

Ala Thr His Tyr Gln Thr Gly Gln Pro Ile Ala Asp Phe Val Lys Gly
225                 230                 235                 240

Asn Arg Tyr Arg Val Ile Gln Val Lys Asp Val Arg Gly Gly Asn Ser
                245                 250                 255

Thr Lys Ala Phe Leu Leu Asp Gly Ile Met Ser Trp Val Trp Glu Gln
                260                 265                 270

Asp Ile Val Glu Ala Gly Gly Gln Ala Val Ala Pro Gln Pro Gln Ala
            275                 280                 285

Lys Lys Trp Tyr Ile Val Leu Pro Ala Asn Ala Thr Ser Trp Thr Val
            290                 295                 300

Tyr Lys Leu Asp Arg Pro Pro Val Lys Ala Asn Lys Ala Asn Ile Ala
305                 310                 315                 320

Gly Thr Leu Arg Pro Ser Lys Phe Gly Gly Leu Thr Tyr Glu Ile Leu
                325                 330                 335

Glu Asp Leu Gly Gly His Val Tyr Lys Ile Arg Thr Gly Asp Phe Gly
            340                 345                 350

Leu Val Lys Ile Tyr Gly Ala Pro Ser Thr Gly Ala Arg Ile Val Glu
                355                 360                 365

Lys
```

<210> SEQ ID NO 9
<211> LENGTH: 996
<212> TYPE: DNA
<213> ORGANISM: Artificial Sequence
<220> FEATURE:
<223> OTHER INFORMATION: Bacteriophage against Geobacillus sp. strain G18

<400> SEQUENCE: 9

```
atggtacaaa tcagacaaat gctagtatca ccacaaaaat accgtattaa atgcccttac    60
gcaatgacgc cagaatatat caccgtccac aacacagcca acgacgcaag cgccaacaac   120
gaggtacaat atatgattca taacagtaac ccagtgtcat ttcatattgc ggttgacgac   180
gtggaggcag ttcaaggatt gccgctagac cgcaacggtt ggcacagtgg agatggtaac   240
ggaccaggaa accgtaaatc aatcggaatc gaaatttgct actcaagaag tggtggggaa   300
cgttaccgga aagccgaacg aaatgcaatt aaactaatcg cgcaactcct gaaagaacgt   360
ggatggggaa ttgaccgtgt gaaaaaacat caagattggt cgggaaagta ttgtccgcac   420
cggatacttg atgaaggacg ttgggaatcg tttaaggcgg aaatacaaaa ggaattaaac   480
ggacagcata cctccgctcc ggtcacacca tcaaccggta atatcggcgt tggttctatc   540
gtcactgtag ccgcacatgc tacgcactat cagacggggc aaccgatagc agattttgtc   600
aagggcaacc ggtacaaagt catacaggta aagatgtgc gtggcggtaa cagtaccaaa    660
gctttttgc tcgacggtat tatgtcgtgg gtgtgggagc aggatattgt cgaggcggga    720
ggacaagcga tagcacccca accgcaggaa aagaaacggt atatcgtgtt gccagcaaac   780
gccactagtt ggacggttta caagcccgac agaccgccag tcaaggcgaa caaagctaat   840
atcgcaggga cgctgagacc gtcaaaattt ggcgggttaa catatgaaat ccttgaggat   900
ttgggcggtt gggtgtttaa aatccggaca ggtgattttg gcttggtaaa aatttacggt   960
gctccaagta caggagcacg gattgtggaa aaataa                             996
```

<210> SEQ ID NO 10
<211> LENGTH: 331
<212> TYPE: PRT
<213> ORGANISM: Artificial Sequence
<220> FEATURE:
<223> OTHER INFORMATION: Bacteriophage against Geobacillus sp. strain G18

<400> SEQUENCE: 10

```
Met Val Gln Ile Arg Gln Met Leu Val Ser Pro Gln Lys Tyr Arg Ile
1               5                   10                  15

Lys Cys Pro Tyr Ala Met Thr Pro Glu Tyr Ile Thr Val His Asn Thr
            20                  25                  30

Ala Asn Asp Ala Ser Ala Asn Asn Glu Val Gln Tyr Met Ile His Asn
        35                  40                  45

Ser Asn Pro Val Ser Phe His Ile Ala Val Asp Asp Val Glu Ala Val
    50                  55                  60

Gln Gly Leu Pro Leu Asp Arg Asn Gly Trp His Ser Gly Asp Gly Asn
65                  70                  75                  80

Gly Pro Gly Asn Arg Lys Ser Ile Gly Ile Glu Ile Cys Tyr Ser Arg
                85                  90                  95

Ser Gly Gly Glu Arg Tyr Arg Lys Ala Glu Arg Asn Ala Ile Lys Leu
            100                 105                 110

Ile Ala Gln Leu Leu Lys Glu Arg Gly Trp Gly Ile Asp Arg Val Lys
        115                 120                 125

Lys His Gln Asp Trp Ser Gly Lys Tyr Cys Pro His Arg Ile Leu Asp
    130                 135                 140

Glu Gly Arg Trp Glu Ser Phe Lys Ala Glu Ile Gln Lys Glu Leu Asn
145                 150                 155                 160

Gly Gln His Thr Ser Ala Pro Val Thr Pro Ser Thr Gly Asn Ile Gly
```

165                 170                 175
Val Gly Ser Ile Val Thr Val Ala Ala His Ala Thr His Tyr Gln Thr
            180                 185                 190

Gly Gln Pro Ile Ala Asp Phe Val Lys Gly Asn Arg Tyr Lys Val Ile
        195                 200                 205

Gln Val Lys Asp Val Arg Gly Gly Asn Ser Thr Lys Ala Phe Leu Leu
    210                 215                 220

Asp Gly Ile Met Ser Trp Val Trp Glu Gln Asp Ile Val Glu Ala Gly
225                 230                 235                 240

Gly Gln Ala Ile Ala Pro Gln Pro Gln Glu Lys Lys Arg Tyr Ile Val
                245                 250                 255

Leu Pro Ala Asn Ala Thr Ser Trp Thr Val Tyr Lys Pro Asp Arg Pro
            260                 265                 270

Pro Val Lys Ala Asn Lys Ala Asn Ile Ala Gly Thr Leu Arg Pro Ser
        275                 280                 285

Lys Phe Gly Gly Leu Thr Tyr Glu Ile Leu Glu Asp Leu Gly Gly Trp
    290                 295                 300

Val Phe Lys Ile Arg Thr Gly Asp Phe Gly Leu Val Lys Ile Tyr Gly
305                 310                 315                 320

Ala Pro Ser Thr Gly Ala Arg Ile Val Glu Lys
                325                 330

<210> SEQ ID NO 11
<211> LENGTH: 944
<212> TYPE: DNA
<213> ORGANISM: Artificial Sequence
<220> FEATURE:
<223> OTHER INFORMATION: Bacteriophage against Geobacillus sp. strain
      G21

<400> SEQUENCE: 11
gtacaaatca gacaaatgct agtatcacca caaaaatacc gtattaaatg cccttacgca    60
atgacgccag aatatatcac cgtccacaac acagccaacg acgcaagcgc caacaacgag   120
gtacaatata tgattcataa cagtaaccca gtgtcatttc atattgcggt tgacgacgtg   180
gaggcagttc aaggattgcc gctagaccgc aacggttggc acagtggaga tggtaacgga   240
ccaggaaacc gtaaatcaat cggaatcgaa atttgctact caagaagtgg tggggaacgt   300
taccggaaag ccgaacgaaa tgcaattaaa ctaatcgcgc aactcctgaa agaacgtgga   360
tggggaattg accgtgtgaa aaaacatcaa gattggtcgg gaaagtattg tccgcaccgg   420
atacttgatg aaggacgttg ggaatcgttt aaggcgaaaa tacaaaagga attaaacgga   480
cagcatacct ccgctccggt cacaccatca accggtaata tcggcgttgg ttctatcgtc   540
actgtagccg cacatgctac gcactatcag acggggcaac cgatagcaga ttttgtcaag   600
ggcaaccggt acaaagtcat acaggtaaaa gatgtgcgtg gcggtaacag taccaaagct   660
tttttgctcg acggtattat gtcgtgggtg tgggagcagg atattgtcga ggcgggagga   720
caagcgatag cacctcaacc gcaggaaaag aaacggtata tcgtgttgcc agcaaacgcc   780
actagttgga cggtttacaa gcccgacaga ccgccagtca aggcgaacaa agctaatatc   840
gcagggacgc tgagaccgtc aaaatttggc gggttaacat atgaaatcct tgaggatttg   900
ggcggttggg tgtttaaatc cggacaggtg attttggctt ggta                    944

<210> SEQ ID NO 12
<211> LENGTH: 314
<212> TYPE: PRT

<213> ORGANISM: Artificial Sequence
<220> FEATURE:
<223> OTHER INFORMATION: Bacteriophage against Geobacillus sp. strain G21

<400> SEQUENCE: 12

```
Val Gln Ile Arg Gln Met Leu Val Ser Pro Gln Lys Tyr Arg Ile Lys
1               5                   10                  15

Cys Pro Tyr Ala Met Thr Pro Glu Tyr Ile Thr Val His Asn Thr Ala
            20                  25                  30

Asn Asp Ala Ser Ala Asn Asn Glu Val Gln Tyr Met Ile His Asn Ser
        35                  40                  45

Asn Pro Val Ser Phe His Ile Ala Val Asp Asp Val Glu Ala Val Gln
    50                  55                  60

Gly Leu Pro Leu Asp Arg Asn Gly Trp His Ser Gly Asp Gly Asn Gly
65                  70                  75                  80

Pro Gly Asn Arg Lys Ser Ile Gly Ile Glu Ile Cys Tyr Ser Arg Ser
                85                  90                  95

Gly Gly Glu Arg Tyr Arg Lys Ala Glu Arg Asn Ala Ile Lys Leu Ile
            100                 105                 110

Ala Gln Leu Leu Lys Glu Arg Gly Trp Gly Ile Asp Arg Val Lys Lys
        115                 120                 125

His Gln Asp Trp Ser Gly Lys Tyr Cys Pro His Arg Ile Leu Asp Glu
    130                 135                 140

Gly Arg Trp Glu Ser Phe Lys Ala Glu Ile Gln Lys Glu Leu Asn Gly
145                 150                 155                 160

Gln His Thr Ser Ala Pro Val Thr Pro Ser Thr Gly Asn Ile Gly Val
                165                 170                 175

Gly Ser Ile Val Thr Val Ala Ala His Ala Thr His Tyr Gln Thr Gly
            180                 185                 190

Gln Pro Ile Ala Asp Phe Val Lys Gly Asn Arg Tyr Lys Val Ile Gln
        195                 200                 205

Val Lys Asp Val Arg Gly Gly Asn Ser Thr Lys Ala Phe Leu Leu Asp
    210                 215                 220

Gly Ile Met Ser Trp Val Trp Glu Gln Asp Ile Val Glu Ala Gly Gly
225                 230                 235                 240

Gln Ala Ile Ala Pro Gln Pro Gln Glu Lys Lys Arg Tyr Ile Val Leu
                245                 250                 255

Pro Ala Asn Ala Thr Ser Trp Thr Val Tyr Lys Pro Asp Arg Pro Pro
            260                 265                 270

Val Lys Ala Asn Lys Ala Asn Ile Ala Gly Thr Leu Arg Pro Ser Lys
        275                 280                 285

Phe Gly Gly Leu Thr Tyr Glu Ile Leu Glu Asp Leu Gly Gly Trp Val
    290                 295                 300

Phe Lys Ser Gly Gln Val Ile Leu Ala Trp
305                 310
```

ENDOLYSIN FROM BACTERIOPHAGE AGAINST *GEOBACILLUS* AND METHODS OF USING

CROSS REFERENCE TO RELATED APPLICATIONS

This application claims benefit under 35 U.S.C. § 119(e) to U.S. Application No. 62/109,156, filed Jan. 29, 2015.

TECHNICAL FIELD

This disclosure generally relates to bacteriophage and endolysins from such bacteriophage.

BACKGROUND

Bacteriophage destroy bacteria but are harmless to humans. They are strain and, usually, species-specific, and they are abundant in nature, in foods, and in the intestinal tract of animals. Bacteriophage are about 100 times smaller than bacteria, and they leave no ecological footprint. Bacteriophage are generally recognized as safe (GRAS).

The lytic lifecycle of bacteriophage typically includes adsorption to a bacterial cell, infection, which includes injecting their nucleic acid into the bacterial cell, replication, maturation, and assembly of bacteriophage inside the bacterial cell. The lytic lifecycle culminates in lysis of the bacterial cell to release all the progeny bacteriophage.

SUMMARY

This disclosure describes bacteriophage against *Geobacillus* and methods of making and using the bacteriophage.

In one aspect, an isolated bacteriophage having lytic activity against *Geobacillus* is provided. Such a bacteriophage typically includes a nucleic acid sequence encoding an endolysin, wherein the nucleic acid sequence has at least 95% sequence identity to a nucleic acid sequence selected to the group consisting of SEQ ID NOs:1, 3, 5, 7, 9, and 11. In some embodiments, the nucleic acid sequence has at least 99% sequence identity to a nucleic acid sequence selected to the group consisting of SEQ ID NOs:1, 3, 5, 7, 9, and 11. In some embodiments, the nucleic acid sequence has a sequence selected to the group consisting of SEQ ID NOs:1, 3, 5, 7, 9, and 11. In some embodiments, the endolysin encoded by the nucleic acid sequence has an amino acid sequence selected from the group consisting of SEQ ID NOs:2, 4, 6, 8, 10, and 12.

In another aspect, an isolated bacteriophage having lytic activity against *Geobacillus* is provided. Such a bacteriophage typically includes a nucleic acid sequence encoding an endolysin having at least 95% sequence identity to an amino acid sequence selected from the group consisting of SEQ ID NOs:2, 4, 6, 8, 10, and 12. In some embodiments, the endolysin has at least 99% sequence identity to an amino acid sequence selected from the group consisting of SEQ ID NOs:2, 4, 6, 8, 10, and 12. In some embodiments, the endolysin has an amino acid sequence selected from the group consisting of SEQ ID NOs:2, 4, 6, 8, 10, and 12.

In still another aspect, an isolated nucleic acid molecule is provided. Typically, the nucleic acid molecule includes a nucleic acid sequence having at least 95% sequence identity to a nucleic acid sequence selected to the group consisting of SEQ ID NOs:1, 3, 5, 7, 9, and 11. In some embodiments, the nucleic acid molecule includes a nucleic acid sequence having at least 99% sequence identity to a nucleic acid sequence selected to the group consisting of SEQ ID NOs:1, 3, 5, 7, 9, and 11. In some embodiments, the nucleic acid molecules Includes a nucleic acid sequence having a nucleic acid sequence selected to the group consisting of SEQ ID NOs:1, 3, 5, 7, 9, and 11. In some embodiments, the nucleic acid molecule encodes a polypeptide having an amino acid sequence selected from the group consisting of SEQ ID NOs:2, 4, 6, 8, 10, and 12.

In yet another aspect, a vector is provided that includes any of the isolated nucleic acids described herein. In another aspect, a host cell is provided that includes such a vector.

In one aspect, a purified polypeptide is provided. Typically, such a polypeptide includes an amino acid sequence having at least 95% sequence identity to an amino acid sequence selected from the group consisting of SEQ ID NOs:2, 4, 6, 8, 10, and 12. In some embodiments, the amino acid sequence has at least 99% sequence identity to an amino acid sequence selected from the group consisting of SEQ ID NOs:2, 4, 6, 8, 10, and 12. In some embodiments, the amino acid sequence has an sequence selected from the group consisting of SEQ ID NOs:2, 4, 6, 8, 10, and 12.

In another aspect, a method of making a polypeptide is provided. Such a method typically includes culturing a host cell as described herein under appropriate conditions.

In still another aspect, a method for reducing the number of viable *Geobacillus* in tobacco is provided. Such a method typically includes contacting tobacco with an effective amount of a composition comprising any of the isolated bacteriophage described herein, any of the isolated nucleic acids described herein, any of the vectors described herein, any of the host cells described herein, or any of the purified polypeptides described herein. In some embodiments, the tobacco is reconstituted leaf.

In yet another aspect, reconstituted tobacco leaf is provided. Such reconstituted tobacco leaf typically includes any of the isolated bacteriophage described herein, any of the isolated nucleic acids described herein, any of the vectors described herein, any of the host cells described herein, or any of the purified polypeptides described herein.

In one aspect, a tobacco product is provided that includes such reconstituted leaf. In some embodiments, the tobacco product is a cigarette.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 1 is a graph showing the effect of the G05 endolysin on *Geobacillus* in culture.

DETAILED DESCRIPTION

A number of bacteria are present on tobacco growing in a field and at various stages of processing. Some of those bacteria are beneficial and, for example, contribute to the flavor profiles of tobacco, while some of those bacteria are undesirable and, for example, damage the tobacco and contribute to unwanted tobacco-specific nitrosamines (TS-NAs). For example, there is at least one unwanted bacteria present on reconstituted leaf (RL) which oftentimes results in a biofilm. The presence of a biofilm on RL can cause holes and result in significant loss of yield. The primary genus of bacteria in the biofilm (about 95%) has been identified as *Geobacillus*.

Bacteriophage Compositions

Isolated bacteriophages are provided herein, as well as progeny thereof. As used herein with respect to bacteriophage, "isolated" refers to a bacteriophage that has been separated from the environment in which it is naturally found (e.g., that does not contain a significant amount of other bacteriophage or of the bacterial host). As used herein, "progeny" refers to replicates of a bacteriophage, including descendants of a bacteriophage created by serial passage or other methods known in the art.

In addition to bacteriophage, a bacteriophage composition also can include media, buffers, one or more nutrients, one or more minerals, one or more co-factors, or any other component that is necessary to maintain viability of the bacteriophage. Additionally, components that are not related to the viability of the bacteriophage may be desirable in a bacteriophage composition such as, without limitation, a dye or color marker.

Bacteriophage Nucleic Acids and Polypeptides

Bacteriophage contain endolysins, a generic term for one or more enzymes that are involved in the degradation of the peptidoglycan in the bacterial cell wall, ultimately resulting in lysis of the bacteria. The specificity exhibited by the bacteriophage for a particular bacteria strain is typically attributed to the endolysin(s). Therefore, as described herein, isolated bacteriophage nucleic acids are provided that encode for the endolysins, and the purified endolysin polypeptides also are provided.

An endolysin gene from a bacteriophage described herein has a nucleic acid sequence shown in SEQ ID NO:1, 3, 5, 7, 9, or 11, and encodes an endolysin polypeptide having a sequence shown in SEQ ID NO:2, 4, 6, 8, 10, or 12, respectively. In addition to a nucleic acid sequence shown in SEQ ID NO:1, 3, 5, 7, 9 or 11, and the polypeptide sequence shown in SEQ ID NO:2, 4, 6, 8, 10 or 12, nucleic acid and polypeptide sequences are provided that differ in sequence from SEQ ID NO:1, 3, 5, 7, 9, or 11, and SEQ ID NO:2, 4, 6, 8, 10, or 12, respectively. For example, nucleic acid sequences having at least 70% sequence identity (e.g., at least 75%, 80%, 85%, 90%, 95%, 99% or 100% sequence identity) to the nucleic acid sequence shown in SEQ ID NO:1, 3, 5, 7, 9, or 11 are provided. Similarly, amino acid sequences having at least 70% sequence identity (e.g., at least 75%, 80%, 85%, 90%, 95%, 99% or 100% sequence identity) to the amino acid sequence shown in SEQ ID NO:2, 4, 6, 8, 10, or 12 are provided.

To calculate the percent sequence identity of two sequences, the first and second sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align differently with other sequences and hence, can have different percent sequence identity values over each aligned region. Two sequences can be aligned to determine percent sequence identity using the algorithm described by Altschul et al. (1997, *Nucleic Acids Res.*, 25:3389-3402), which is incorporated into BLAST (basic local alignment search tool) programs available at ncbi.nlm.nih.gov on the World Wide Web.

With respect to nucleic acids, an "isolated" nucleic acid refers to a nucleic acid that is separated from other nucleic acids that are usually associated with the isolated nucleic acid. Thus, an "isolated" nucleic acid includes, without limitation, a nucleic acid that is free of sequences that naturally flank one or both ends of the nucleic acid in the genome of the organism from which the isolated nucleic acid is derived (e.g., a cDNA or genomic DNA fragment produced by PCR or restriction endonuclease digestion). In addition, an isolated nucleic acid molecule can include an engineered nucleic acid molecule such as a recombinant or a synthetic nucleic acid molecule. With respect to polypeptides, a "purified" polypeptide refers to a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the proteins and naturally occurring molecules with which it is naturally associated. Since a polypeptide that is chemically synthesized is, by nature, separated from the components that naturally accompany it, a synthetic polypeptide is "purified."

The nucleic acids described herein (e.g., encoding the bacteriophage endolysin polypeptide) can be introduced into vectors. Vectors, including expression vectors, are commercially available or can be produced by routine molecular biology methods. A vector containing a bacteriophage nucleic acid also can have elements necessary for expression operably linked to the bacteriophage nucleic acid, and a vector further can include sequences such as those encoding a selectable marker (e.g., an antibiotic resistance gene) and/or sequences that can be used in purification of a polypeptide (e.g., 6×His tag).

Elements necessary for expression include nucleic acid sequences that direct and regulate expression of nucleic acid coding sequences such as, for example, promoter sequences. Elements necessary for expression also can include introns, enhancer sequences, response elements, or inducible elements that modulate expression of a nucleic acid. As used herein, operably linked means that an element necessary for expression (e.g., a promoter and/or other regulatory element) is positioned in a vector relative to a nucleic acid coding sequence in such a way as to direct or regulate expression of the nucleic acid coding sequence.

Vectors containing a bacteriophage nucleic acid can be introduced into host cells. Methods of introducing nucleic acids into host cells are known in the art and include, without limitation, calcium phosphate precipitation, electroporation, heat shock, lipofection, microinjection, and viral-mediated nucleic acid transfer. The term "host cell" refers not only to the particular cell but also to the progeny or potential progeny of such a cell. A host cell can be any prokaryotic or eukaryotic cell. For example, nucleic acids can be expressed in bacterial cells such as, without limitation, *E. coli*, or in insect cells, yeast cells, or mammalian cells such as Chinese hamster ovary (CHO) cells or COS cells. It would be appreciated by those skilled in the art that the natural infection process of bacteriophage can be used to introduce a nucleic acid or nucleic acid vector into a bacterial cell.

Methods of Using a Bacteriophage Composition and Bacteriophage Nucleic Acid and Polypeptide The bacteriophage described herein, or the bacteriophage endolysin nucleic acid or polypeptide described herein, can be used in methods of reducing the number and/or growth of the *Geobacillus* bacteria on reconstituted leaf (or on any of the tobacco materials used to make reconstituted leaf), which reduces the resulting *Geobacillus*-produced biofilm on the reconstituted leaf. For example, reconstituted leaf can be contacted with the bacteriophage at any point during the process of making the reconstituted leaf or after the reconstituted leaf has been produced. In certain instances, the tobacco material (e.g., tobacco stems, tobacco leaves, tobacco solubles) can be contacted with the bacteriophage prior to being used in or made into reconstituted leaf. Contacting reconstituted leaf (or tobacco material prior being made into reconstituted leaf) with the bacteriophage described herein reduces the amount of biofilm present on the reconstituted leaf. Since the presence of biofilm results in holes in the reconstituted leaf, the treated reconstituted leaf has fewer holes, which increases yield and decreases waste.

Since biofilm is present in a number of different environments (e.g., hospitals, kitchens, bathrooms, in fluid-carrying pipes (e.g., carrying water, milk, oil, fuel, or sewage), on boat hulls, on plants or trees, in the oral cavities of animals, and/or in paper- or pulp-making facilities), and since at least a portion of this biofilm is *Geobacillus*-produced biofilm, the bacteriophage described herein can be used to reduce or eliminate the biofilm that is present in these different environments.

As used herein, a reduction (e.g., a statistically significant reduction) in the number of viable bacteria means a reduction in the number of bacteria that are alive and capable of, for example, replication. For example, lysed bacteria or bacteria in the process of lysing are not considered viable. The viability of bacteria can be determined using methods routinely used in microbiology. In addition, preventing or reducing the amount of biofilm means that the surface area containing biofilm is reduced or the volume of the biofilm on a surface is reduced relative to a "control" surface that has not been contacted with a bacteriophage. These reductions (i.e., in the number of viable bacteria or the amount of biofilm) in the presence of any of the bacteriophage (or endolysin nucleic acid or polypeptide) described herein are a result of the lytic activity exerted by the bacteriophage (or endolysin nucleic acid or polypeptide) on the bacteria. As used herein, an "effective amount" of a bacteriophage or of an endolysin nucleic acid or polypeptide is an amount that results in lysis of bacteria in an amount or at a rate that is sufficient to reduce the number of viable bacteria or the amount of biofilm present to a desired level. As used herein, "statistically significantly" refers to a p-value of less than 0.05 (e.g., less than 0.025 or 0.01) using an appropriate measure of statistical significance (e.g., a one-tailed two-sample t-test).

Methods of Obtaining Bacteriophage Compositions

Methods of obtaining bacteriophage are known in the art. See, for example, *Bacteriophages: Methods and Protocols*, Volume 1: Isolation, Characterization, and Interactions (Methods in Molecular Biology), Eds, Clokie & Kropinski, 2010, Humana Press; Seeley et al., 1982, J. Applied Bacteriol., 53:1-17; Pope et al., 2011, PLoS ONE, 6:e16329; and Hendrix et al., 1999, PNAS USA, 96:2192-7. Briefly, bacteria of interest (e.g., the target bacteria) are obtained, generally using standard culture methods. Typically, bacteria are cultured in such as way so as to activate the lytic phase of bacteriophage native to the bacteria and cause lysis. Following lysis of the bacteria, the bacteriophage is collected and can be characterized using any number of known methods such as, without limitation, nucleic acid sequencing, electron microscopy, burst size, and/or attachment rate. Bacteriophage also can be described based on their host (i.e., host profiling).

Tobacco Products

Tobacco products for adult tobacco consumers are provided that contain tobacco (e.g., whole leaf, stems, cut, chopped or comminuted leaf or stem, or reconstituted leaf) that has been contacted with one or more bacteriophage (or endolysin nucleic acids or polypeptides). In some instances, the one or more bacteriophage include the bacteriophage described herein.

Under certain circumstances, the tobacco or reconstituted leaf can undergo one or more treatments in order to remove or inactivate the bacteriophage once the amount and/or growth of the respective bacteria has reached an acceptable level. However, since bacteriophage are in the generally recognized as safe (GRAS) category, the bacteriophage may be present in the final tobacco product.

Tobacco products are known in the art and include any product made or derived from tobacco that is intended for human consumption, including any component, part, or accessory of a tobacco product. Representative tobacco products include, without limitation, smokeless tobacco products, tobacco-derived nicotine products, cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, and cut tobacco. Representative smokeless tobacco products include, for example, chewing tobacco, snus, pouches, films, tablets, coated dowels, rods, and the like. Representative cigarettes and other smoking articles include, for example, smoking articles that include filter elements or rod elements, where the rod element of a smokeable material can include cured tobacco within a tobacco blend. In addition to the tobacco described herein (i.e., that includes one or more bacteriophages), tobacco products also can include other ingredients such as, without limitation, binders, plasticizers, stabilizers, and/or flavorings. See, for example, US 2005/0244521, US 2006/0191548, US 2012/0024301, US 2012/0031414, and US 2012/0031416 for examples of tobacco products. Suitable packaging is known for the various types of tobacco products.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Bacteriophage Endolysins

*Geobacillus* bacteriophages isolated by Micreos BV (The Netherlands), designated G01-G09, were sequenced to determine the sequence identity among the bacteriophages and to identify the endolysin sequence from each. Six of the nine bacteriophages had readily identifiable endolysin sequences. Out of the 6 endolysins identified, 3 were 99% similar (G05, G08, G09). The sequences of the endolysins are shown in the attached Appendix A.

Example 2—Cloning and Expression of the Endolysin Gene

The endolysin gene from G05 was then cloned into an expression vector using conventional PCR techniques, and the expression vector was transformed into BL21-AI™ ONESHOT® Chemically Competent *E. coli* cells. Following expression, the protein was isolated and run on an SDS-PAGE gel.

Given the homology between the endolysin gene of G05 and the endolysin gene of G08 and G09, the same PCR conditions, including primer sequences, were used to clone the endolysin gene from each of the G05, G08 and G09 bacteriophages.

Example 3—Evaluating Endolysin Activity

The transformed organisms containing the endolysin gene are applied to *Geobacillus* in pure culture, in strong brown water (SBW), and on tobacco matrices to test the efficacy of the endolysin on bacterial cell lysis. The purified protein is used in various tobacco matrices such as reconstituted leaf (RL) to prevent biofilm formation.

Example 4—Use of Bacteriophage in Reconstituted Leaf (RL)

*Geobacillus* is a biofilm-producing bacterial organism that is obligately thermophilic and facultatively anaerobic. When it produces a biofilm on tobacco (e.g., reconstituted leaf), the congealed material interferes with the further processing of the tobacco.

To determine the effectiveness of the bacteriophage against *Geobacillus* as described herein, the bacteriophage was inoculated into fresh 1/10 Tryptic Soy Broth (TSB) with Yeast Extract (YE), collectively "TSBYE," and incubated at 55° C. for up to four hours (OD between 0.5 and 0.9). The culture was then inoculated into fresh TSBYE containing either 1:1 or 1:10 ratio of Phage:TSBYE, SM Buffer:TSBYE (negative control), and TSBYE. The mixtures were incubated at 55° C. overnight and then serially diluted 1/10 to $10^{-5}$, and plated in duplicate on Tryptic Soy Agar with Yeast Extract (TSAYE). The plates were incubated at 60° C. overnight. The addition of the phage inhibited the growth of *Geobacillus*.

Samples from the reconstituted leaf process were collected and stored at 4° C. (native) or sterilized by passing sequentially through 0.45 micron and 0.22 micron filters and stored at 4° C. (sterile). The samples were then inoculated with mid-log phase *Geobacillus*, SM buffer (negative control) or the bacteriophage. The samples were also supplemented with TSBYE to allow for growth. The mixtures were incubated at 55° C. overnight and then serially diluted 1/10 to $10^{-5}$, and plated in duplicate on TSAYE. The plates were incubated at 60° C. overnight. Results showed that the phage inhibited the growth of *Geobacillus*.

To determine the effectiveness of the cloned endolysin against *Geobacillus* described herein was inoculated into fresh TSBYE and incubated at 55 C for up to four hours (i.e., to an OD of between 0.5 and 0.9). A 1:10 inoculation of the culture was transformed into fresh TSBYE containing endolysin with a range of 0 to 200 μg/ml. The prepared samples were then placed in a microplate reader and monitored for growth at an $OD_{600}$ for 24 hours at 50 C. Readings were taken every 20 minutes with shaking between each reading. See FIG. 1.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method for reducing the *Geobacillus*-produced biofilm on tobacco, comprising:
contacting said tobacco with a composition comprising a polypeptide having at least 95% sequence identity to an amino acid sequence selected from the group consisting of SEQ ID NO:2, 4, 6, 8, 10 and 12, wherein said tobacco is reconstituted leaf.

2. The method of claim 1, wherein the polypeptide has at least 99% sequence identity to an amino acid sequence selected from the group consisting of SEQ ID NO:2, 4, 6, 8, 10 and 12.

3. The method of claim 1, wherein the polypeptide has the amino acid sequence selected from the group consisting of SEQ ID NO:2, 4, 6, 8, 10 and 12.

4. The method of claim 1, wherein the polypeptide is encoded by a nucleic acid having at least 95% sequence identity to a sequence selected from the group consisting of SEQ ID NO:1, 3, 5, 7, 9 and 11.

5. The method of claim 1, wherein the polypeptide is encoded by a nucleic acid having at least 99% sequence identity to a sequence selected from the group consisting of SEQ ID NO:1, 3, 5, 7, 9 and 11.

6. The method of claim 1, wherein the polypeptide is encoded by a nucleic acid having the sequence shown in a sequence selected from the group consisting of SEQ ID NO:1, 3, 5, 7, 9 and 11.

7. The method of claim 1, wherein the polypeptide is comprised within a bacteriophage.

8. The method of claim 1, wherein said method reduces the surface area of said *Geobacillus*-produced biofilm present on said reconstituted leaf as compared to an untreated control.

9. The method of claim 1, wherein said method reduces the volume of said *Geobacillus*-produced biofilm present on said reconstituted leaf as compared to an untreated control.

10. The method of claim 1, wherein said reconstituted leaf comprises fewer holes as compared to an untreated control.

11. The method of claim 1, wherein said polypeptide is synthetically produced.

12. The method of claim 1, wherein said contacting occurs during the process of making said reconstituted leaf.

13. The method of claim 1, wherein said contacting occurs after said reconstituted leaf has been produced.

* * * * *